United States Patent
Conoci et al.

(10) Patent No.: US 9,434,987 B2
(45) Date of Patent: Sep. 6, 2016

(54) LAB ON CHIP CARTRIDGE

(71) Applicant: STMicroelectronics, S.r.l., Agrate Brianza (IT)

(72) Inventors: Sabrina Conoci, Tremestieri Etneo (IT); Maria Eloisa Castagna, Catania (IT); Massimo Orazio Spata, Catania (IT); Dario Russo, Cerano (IT)

(73) Assignee: STMicroelectronics S.r.l., Agrate Brianza (IT)

( * ) Notice: Subject to any disclaimer, the term of this patent is extended or adjusted under 35 U.S.C. 154(b) by 177 days.

(21) Appl. No.: 14/543,276

(22) Filed: Nov. 17, 2014

(65) Prior Publication Data

US 2015/0140563 A1  May 21, 2015

(30) Foreign Application Priority Data

Nov. 20, 2013  (IT) .............................. TO2013A0940

(51) Int. Cl.
*B01L 7/00* (2006.01)
*C12Q 1/68* (2006.01)
(Continued)

(52) U.S. Cl.
CPC ......... *C12Q 1/6851* (2013.01); *B01L 3/50851* (2013.01); *C12Q 1/686* (2013.01); *C12Q 1/6825* (2013.01); *G01N 21/6452* (2013.01); *G06K 9/0014* (2013.01); *G06T 7/0012* (2013.01); *G06T 7/0014* (2013.01); *B01L 7/52* (2013.01); *B01L 2200/10* (2013.01); *B01L 2200/12* (2013.01); *B01L 2300/0816* (2013.01); *B01L 2300/0819* (2013.01); *B01L 2300/0829* (2013.01); *B01L 2300/0851* (2013.01); *B01L 2300/0887* (2013.01); *B01L 2300/0893* (2013.01); *B01L 2300/161* (2013.01); *B01L 2300/163* (2013.01); *B01L 2300/168* (2013.01); *B01L 2300/1827* (2013.01); *G01N 21/01* (2013.01); *G01N 21/0303* (2013.01);
(Continued)

(58) Field of Classification Search
CPC .... G01N 21/01; G01N 21/253; G01N 21/51; B01L 2200/10; B01L 2200/12; B01L 2300/0816; B01L 2300/0819; B01L 2300/0829; B01L 2300/0851; B01L 2300/0887; B01L 2300/0893; B01L 2300/161; B01L 2300/163; B01L 2300/168; B01L 2300/01
See application file for complete search history.

(56) References Cited

U.S. PATENT DOCUMENTS 6,018,388 A * 1/2000 Nawracala ............ B01L 3/5085
356/246
6,839,454 B1 1/2005 Park
(Continued)

OTHER PUBLICATIONS

Canny, "A Computational Approach to Edge Detection," *IEEE Transactions on Pattern Analysis and Machine Intelligence* PAMI-8(6):679-698, Nov. 1986.
(Continued)

*Primary Examiner* — Jennifer Wecker
(74) *Attorney, Agent, or Firm* — Seed IP Law Group PLLC

(57) ABSTRACT

A cartridge for an optical analysis, including a supporting body, having a first face and a second face opposite to one another; a plurality of wells adapted to receive a biological solution to be analyzed, the wells extending in the supporting body on the first face; at least one biocompatible layer extending inside each well; an anti-reflection layer extending on the first face outside the wells; and a reflection layer extending inside each well. Methods of using same are also provided.

25 Claims, 8 Drawing Sheets

(51) Int. Cl.
*G01N 21/01* (2006.01)
*B01L 3/00* (2006.01)
*G01N 21/64* (2006.01)
*G06T 7/00* (2006.01)
*G06K 9/00* (2006.01)
G01N 21/25 (2006.01)
G01N 21/51 (2006.01)
G01N 21/03 (2006.01)

(52) U.S. Cl.
CPC ............ *G01N21/253* (2013.01); *G01N 21/51* (2013.01); *G06T 2207/10064* (2013.01); *G06T 2207/20024* (2013.01); *G06T 2207/20061* (2013.01); *G06T 2207/30072* (2013.01); *Y10T 29/49885* (2015.01)

(56) References Cited

U.S. PATENT DOCUMENTS

| | | | |
|---|---|---|---|
| 2003/0027022 A1* | 2/2003 | Arana | B01F 5/0618 429/416 |
| 2003/0092194 A1 | 5/2003 | Gambini et al. | |
| 2004/0208350 A1 | 10/2004 | Rea et al. | |
| 2005/0170498 A1 | 8/2005 | Dolley et al. | |
| 2007/0154357 A1* | 7/2007 | Szlosek | B01L 3/5085 422/566 |
| 2010/0142848 A1 | 6/2010 | Kolterman et al. | |
| 2011/0285837 A1 | 11/2011 | Bello et al. | |
| 2012/0108454 A1 | 5/2012 | Alessi et al. | |
| 2012/0170608 A1 | 7/2012 | Bianchessi et al. | |
| 2013/0004952 A1 | 1/2013 | Castagna et al. | |
| 2013/0004954 A1 | 1/2013 | Bianchessi et al. | |
| 2013/0176556 A1* | 7/2013 | Larkin | G01N 21/01 356/73 |

OTHER PUBLICATIONS

Horsthemke et al., "DNA Microarray Spot Detection Using Hough Transforms," CTI Research Symposium, Jan. 1, 2006, retrieved from: URL=http://facweb.cs.depaul.edu/research/vc/publications/CTI_Research_Symposium2006?HorsthemkeTA.pdf, 5 pages.

Liu et al., "Validation of a quantitative method for real time PCR kinetics," *Biochemical and Biophysical Research Communications* 294:347-353, 2002.

Rutledge, "Sigmoidal curve-fitting redefines quantitative real-time PCR with the prospective of developing automated high-throughput applications," *Nucleic Acids Research* 32(22):e178, 8 pages.

Spiess et al., "Highly accurate sigmoidal fitting of real-time PCR data by introducing a parameter for asymmetry," *BMC Bioinformatics* 9:221, 2008, 12 pages.

* cited by examiner

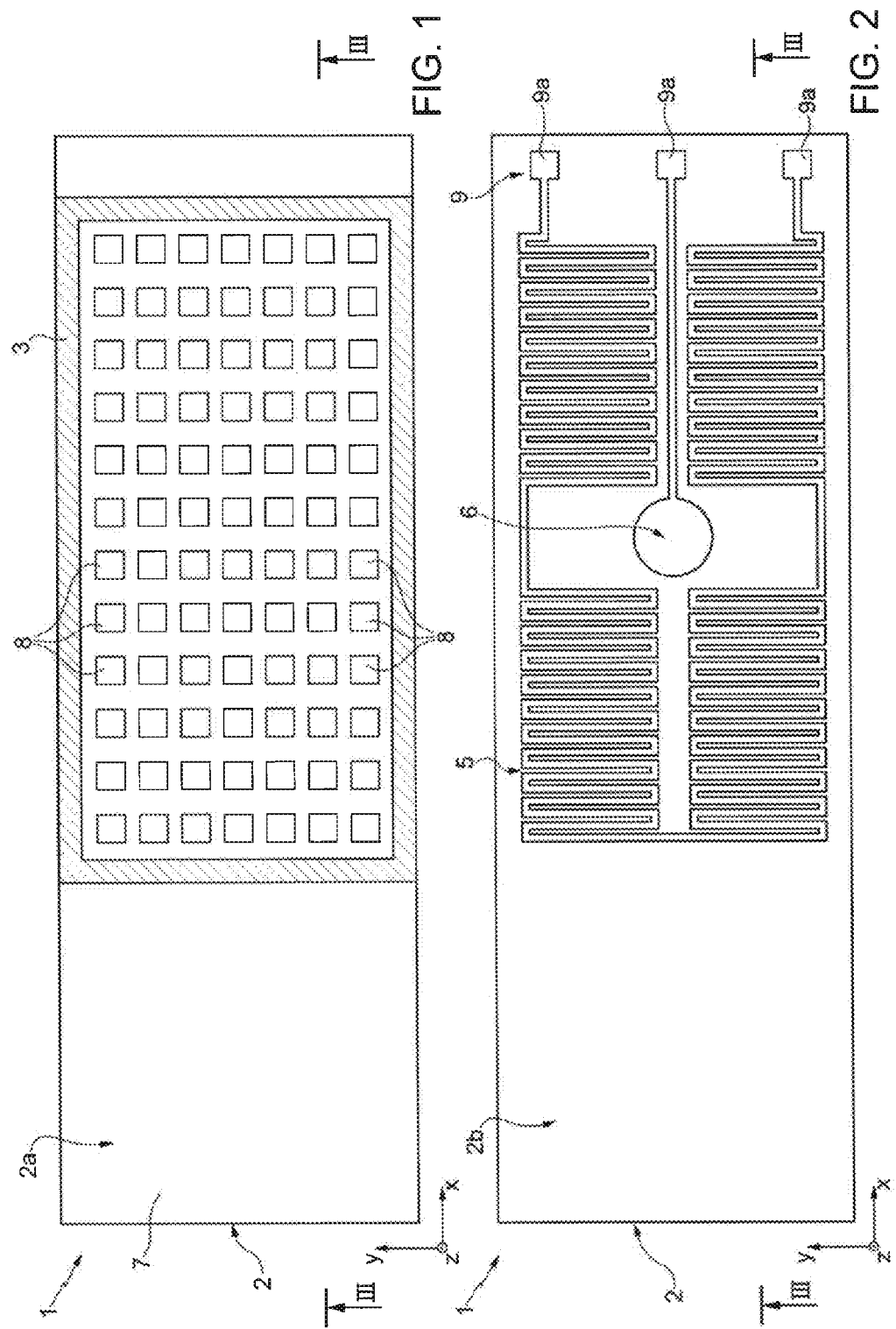

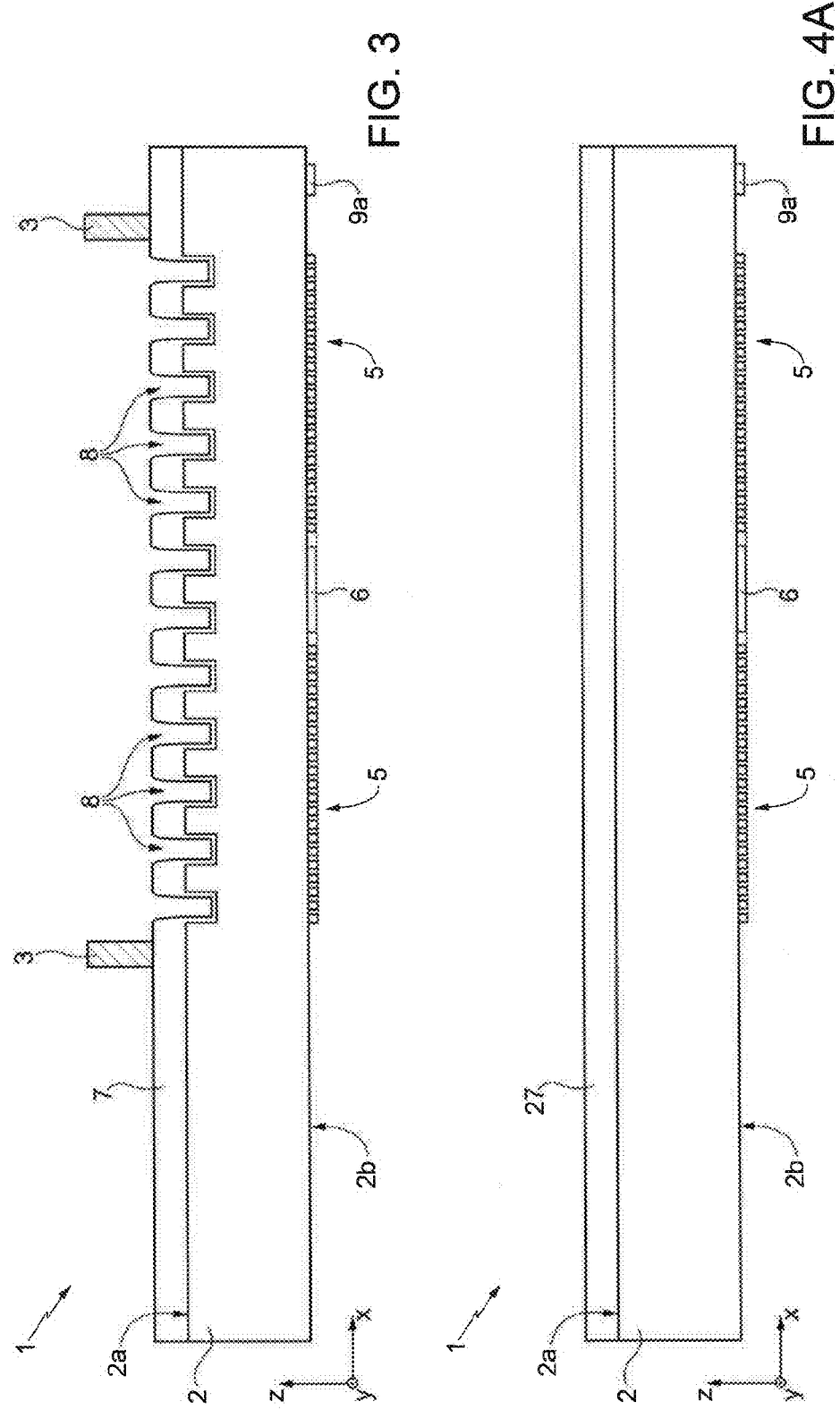

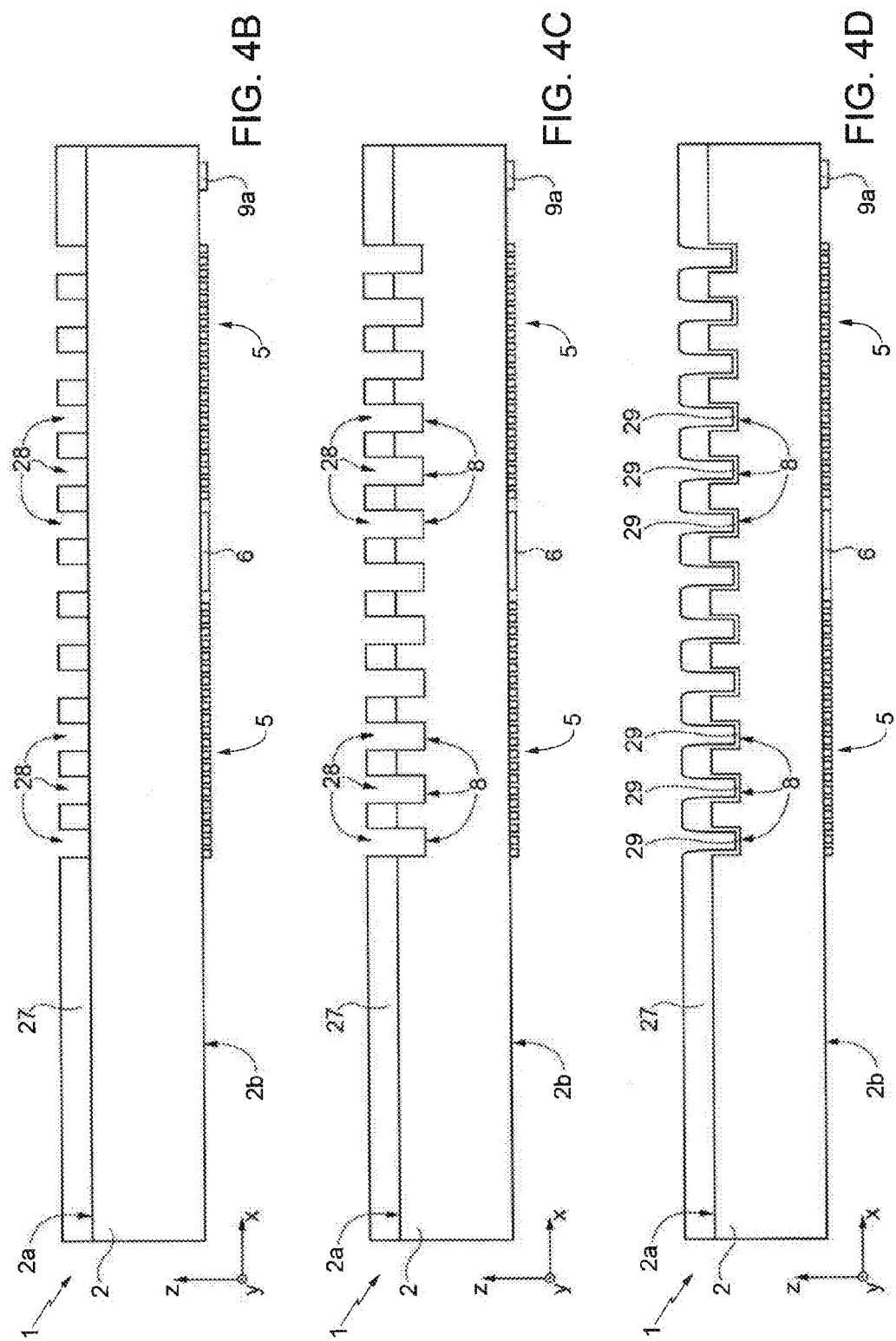

LAB ON CHIP CARTRIDGE

PRIOR RELATED APPLICATIONS

This application claims priority to TO2013A000940, filed Nov. 20, 2013, and incorporated by reference herein in its entirety for all purposes.

FIELD OF THE DISCLOSURE

The present disclosure relates to methods, systems or kits for the quantitative analysis of reactions occurring in a chip or other microfluidic device, in particular to a method of image analysis.

BACKGROUND OF THE DISCLOSURE

As is known, the analysis of nucleic acids requires preliminary steps of preparation of a specimen of biological material, amplification of the nucleic material contained therein, and hybridization of individual target strands or reference strands, corresponding to the sequences sought. At the end of these preparatory steps, the specimen may also be examined to check whether the amplification has been carried out correctly.

According to the methodology referred to as "real-time polymerase-chain-reaction" or "PCR", the DNA is amplified through thermal cycles appropriately selected, and the progress of the amplification is detected and monitored by fluorescence during the entire process.

Various methods and apparatuses for inspection of an optical type are known for this purpose. In particular, the methods and apparatuses of an optical type are frequently based upon the phenomenon of fluorescence. The amplification reactions are conducted so that the nucleic acid strands, contained in a recognition chamber provided in a support, include fluorescent molecules or fluorophores. The support is exposed to a light source having an appropriate spectrum of emission, such as to excite the fluorophores. In turn, the excited fluorophores emit a secondary radiation at a wavelength of emission higher than the peak of the excitation spectrum. The light emitted by the fluorophores is collected and detected by an optical sensor. In order to eliminate the background light radiation, which represents a source of noise, the optical sensor is provided with bandpass filters centered at the wavelength of emission of the fluorophores.

The detection of different substances in the same specimen normally requires the use of distinct fluorophores, which have respective excitation and emission wavelengths. Light sources with different emission spectra are then used in succession, for analyzing the responses in the excitation and emission bands of each fluorophore.

PCR analyzers designed for being used for optical reading of the specimens are described in the documents Nos. US20120170608 and US20130004954. These analyzers are designed to read supports provided with a relatively small number of wells (in particular, six wells) containing the specimens for being analyzed, and each well has relatively large dimensions; i.e., it has a square or round shape with a side or diameter between 3 and 4 mm.

Other biochemical and chemical analyses may be similar, sometimes substituting an antibody for the detection of proteins, or other ligands for the detection of other chemicals. However, many are also amendable to a fluorescence-based analysis.

Known systems present some limitations. In particular, the composition of the surface of the chip typically used for analysis generates undesirable reflections of the optical source used for illuminating the support during fluorescence analysis, generating background noise that raises the detection-sensitivity threshold.

Furthermore, the present applicant has found that the systems described in the documents Nos. US20120170608 and US20130004954 do not enable optical reading of supports of silicon having wells of dimensions smaller than those envisaged by the known art described therein (for example, square wells with a side equal to or smaller than 1 mm). Images, typically low-resolution ones (e.g., 300×200 pixels), made by such systems create difficulty in the discrimination of the individual wells and in selective acquisition of the brightness of the fluorescence emitted by the wells. In conclusion, a reading based upon analysis of the fluorescence of said supports is, in effect, impracticable for values of fluorescence below a certain threshold that are typical of a real-time PCR, antibody detection or otherwise.

Analysis on such small volumes envisages use of high-resolution image-acquisition systems, or a modification of the light-emission sources and an increase of the cost and size of the reading apparatus, which is undesirable as increasing cost.

Thus, what is needed in the art are better devices and methods for the collection and analysis of image date when available from a tiny well or other site.

SUMMARY OF THE DISCLOSURE

The aim of the present disclosure is to provide a kit and devices for biochemical analyses and a method for carrying out a biochemical process that will enable the limitations described above for being overcome and, in particular, that will enable reduction of the risk of reading errors during said analysis.

According to the present disclosure, a kit and device for biochemical analyses and a method for carrying out a biochemical process are provided, as defined in the annexed claims.

For example, an optical analyzer is configured to carry out fluorescence analysis of a plurality of small wells. The analyzer comprises a control unit (microprocessor and memory) configured to: (a) acquire an image associated with the fluorescence emitted by the cartridge; (b) identify, in the image, pixels belonging to boundary lines of the wells by generating a black and white binary image; (c) recognize, between the geometrical shapes identified in step (b), the ones that best approximate a reference geometrical shape identifying an ideal well; (d) acquire, from the starting image, values of light intensity only in portions of the image itself that in turn correspond to the regions recognized in step (c); and, (e) evaluate a state of advance and/or a result of the biochemical analysis on the basis of the values of light intensity acquired in step (d).

Advantageously, the interwell regions are coated with an anti-reflective layer, such as described herein, providing less interference from random reflections off the cartridge. For example, the effective thickness h of the passivation layer outside the wells is thus chosen between $\lambda_E \cos \theta/(4 \cdot n) - 10\%$ and $\lambda_E \cos \theta/(4 \cdot n) + 10\%$, preferably $\lambda_E \cos \theta/(4 \cdot n)$, whereas inside the wells is chosen different from $\lambda_E/(4 \cdot n)$, for example less than $\lambda_E/(4 \cdot n)$, where n is the index of refraction of the passivation layer and $\theta$ is the angle formed with the normal to the plane of incidence of the radiation and $\lambda_E$ is the wavelength of exciting light.

The disclosure includes the following embodiments in any combination of one or more thereof:

A cartridge for an optical analysis, comprising:
a supporting body, having a first face and a second face opposite to one another;
a plurality of wells adapted to receive a biological solution to be analyzed, said wells extending in said supporting body on said first face;
at least one biocompatible layer extending inside each well;
an anti-reflection layer extending on said first face outside said wells; and
a reflection layer extending inside each well.
A cartridge as herein described, wherein said anti-reflection layer has:
a thickness of approximately one quarter of a excitation wavelength ($\lambda_{E1}$) divided by the refractive index of the anti-reflection layer, or
equal to an odd multiple of one quarter of the excitation wavelength divided
by the refractive index of the respective anti-reflection layer, and multiplied
by the cosine of the angle that is formed with the normal to the plane of incidence of a radiation having the excitation wavelength ($\lambda_{E1}$), and
wherein said reflection layer has a thickness smaller than one quarter of the
excitation wavelength ($\lambda_{E1}$) divided by the refractive index of the respective
biocompatible layer and multiplied by the cosine of the angle that is formed
with the normal to the plane of incidence of the radiation having the excitation wavelength ($\lambda_{E1}$).
A cartridge as herein described, wherein said reflection layer and said biocompatible layer coincide.
A cartridge as herein described, wherein said biocompatible layer, said reflection layer and said anti-reflection layer are made of silicon oxide.
A cartridge as herein described, wherein said one or more biocompatible layers includes a silicon oxide layer covered with Bovine Serum Albumin.
A cartridge as herein described, further comprising an on-board containment
module coupled to the first face of the supporting body at edge regions of the first face for completely surrounding said plurality of wells.
A cartridge as herein described, further comprising at least one heater thermally coupled to the plurality of wells by means of the supporting body.
A cartridge as herein described, further comprising a temperature sensor thermally coupled to the supporting body.
A cartridge as herein described, wherein each well of said cartridge comprises nucleic-acid probes for hybridization to respective target nucleic acids, and a solution containing two primers capable of binding to a target nucleic acids, nucleotides, nucleic-acid extender enzymes and said target nucleic acids, and said solution being uniformly covered by mineral oil for countering evaporation of said solution.
A method of manufacturing a cartridge for an optical process, comprising:
forming a plurality of wells adapted to receive a sample to be analyzed in a
supporting body having a first face and a second face opposite to one another, said wells extending in said supporting body on said first face;
forming at least one biocompatible layer extending inside each well;
forming an anti-reflection layer extending on the first face outside said wells; and forming a reflection layer extending inside each well.
A method as herein described, wherein said anti-reflection layer has i) a thickness of approximately one quarter of an excitation wavelength ($\lambda_{E1}$) divided by the refractive index of the anti-reflection layer, or ii) equal to an odd multiple of one quarter of the excitation wavelength divided by the refractive index of the respective anti-reflection layer, and multiplied by the
cosine of the angle that is formed with the normal to the plane of incidence
of the radiation having the excitation wavelength ($\lambda_{E1}$), and wherein
said reflection layer has a thickness smaller than one quarter of the excitation wavelength ($\lambda_{E1}$) divided by the refractive index of the respective biocompatible layer and multiplied by the cosine of the angle that is formed with the normal to the plane of incidence of the radiation having the excitation wavelength ($\lambda_{E1}$).
A method as herein described, further comprising the step of rendering the biocompatible layer hydrophilic.
A method as herein described, wherein rendering the biocompatible layer hydrophilic includes:
depositing a silicon dioxide layer in said wells;
treating the silicon dioxide layer using a solution of $CH_3OH:HCl$;
rinsing the treated silicon dioxide layer with water; and
carrying out an anhydrification step.
A method as herein described, wherein treating the silicon dioxide layer using a solution of $CH_3OH:HCl$ comprises treating the silicon dioxide layer using a solution of $CH_3OH:HCl$ (4:1) for 10 minutes at room temperature; wherein rinsing comprises rinsing with ultra-pure water at pH 7.0 for removing the reagents in excess; and wherein the anhydrification
step comprises a thermal treatment in an oven for 15 minutes at 70° C.
A method as herein described, wherein the steps of forming said reflection layer and said biocompatible layer are carried out in single step deposition step.
A method as herein described, wherein forming said biocompatible layer, said reflection layer and said anti-reflection layer includes depositing silicon
oxide.
A method as herein described, wherein forming at least one biocompatible layer includes:
depositing a silicon dioxide layer in said wells; and
treating said dioxide layer with a solution including 1% bovine serum albumin, 5% sodium chloride plus sodium citrate.
A method as herein described, wherein treating step is performed at 55° C. for a time of between 4 and 15 hours, the method further comprising washing with deionized water.
A method as herein described, further comprising forming an on-board containment module coupled to the first face of the supporting body at edge
regions of the first face for completely surrounding said plurality of wells.
A method as herein described, further comprising forming at least a heater thermally coupled to the plurality of wells by means of the supporting body.
A method as herein described, further comprising forming a temperature sensor thermally coupled to the supporting body.
A method of PCR analysis, said method comprising:
adding nucleic-acid probes to each well of the cartridge as herein described;
adding a solution containing two primers capable of binding to a target nucleic acid, nucleotides, nucleic-acid extender enzymes and a sample nucleic acid containing a target nucleic acid to each of said wells;
performing a plurality of thermal cycles in said wells to amplify said target
nucleic acid; and detecting hybridization of said amplified nucleic acid to said nucleic acid probes in each of said wells.
A PCR method, further comprising the step of covering said wells with wax or mineral oil during said thermal cycles.
A PCR method, wherein said detecting step d occurs in each thermal cycle.
A PCR method further comprising the steps of:
supplying a sample biological specimen; and
extracting, from said sample biological specimen said sample nucleic acid.

DESCRIPTION OF FIGURES

For a better understanding of the invention, some embodiments thereof will now be described purely by way of non-limiting example and with reference to the attached drawings, wherein:

FIG. 1 is a top plan view of a cartridge for biochemical analyses according to an embodiment of the present invention.

FIG. 2 is a bottom plan view of the cartridge of FIG. 1.

FIG. 3 is a lateral view of the cartridge of FIG. 1, sectioned along the plane of trace III-III of FIG. 1.

FIG. 4A-4D show, in lateral cross-sectional view, steps for manufacturing the cartridge of FIG. 1-3;

DETAILED DESCRIPTION

Figure 5:
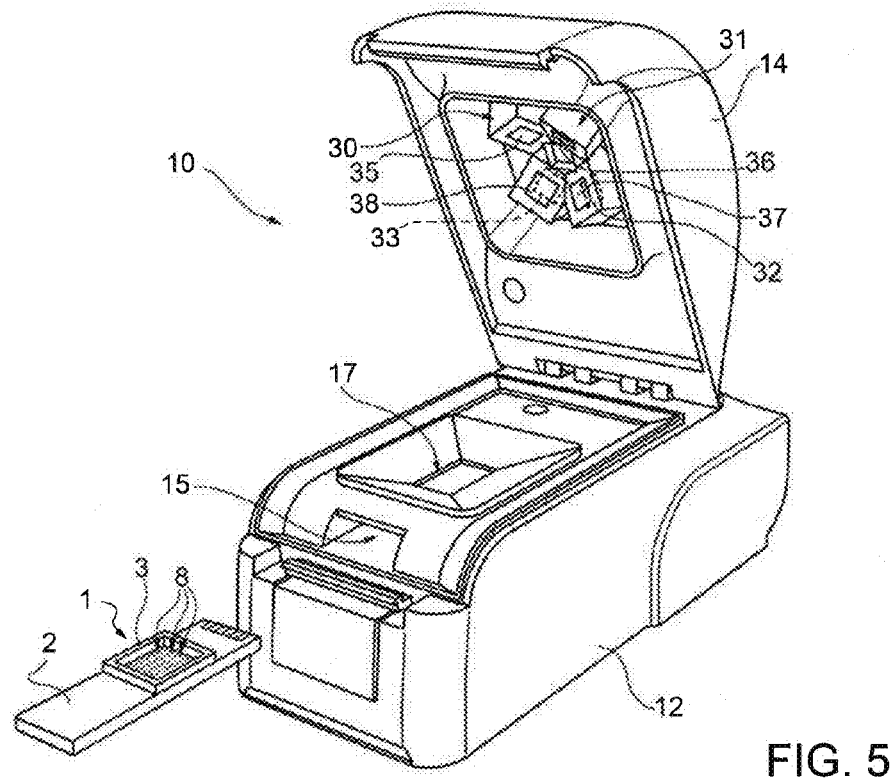
FIG. 5 is a perspective view of an analyzer for biochemical analyses.

According to one aspect of the present disclosure, an optical analyzer is provided, configured to receive a cartridge for biochemical analyses including a plurality of wells, and carry out fluorescence analysis of said cartridge, in particular of the wells. The analyzer comprises a control unit (microprocessor and memory) configured to: (a) acquire an image associated to the fluorescence emitted by the cartridge (in particular, by the wells); (b) identify, in the image, pixels belonging to boundary lines of the wells by generating a binary image, i.e., an image represented with just two levels of color, black and white; (c) recognize, from among the geometrical shapes identified in step (b), the ones that best approximate (or resemble) a reference geometrical shape identifying an ideal well (this step is performed, in particular by a Hough filter); (d) acquire, from the starting image, values of light intensity (identifying the fluorescence emitted by the wells) only in portions of the image itself that in turn correspond to the regions recognized in step (c); and (e) evaluate a state of advance and/or a result of the biochemical analysis on the basis of the values of light intensity acquired in step (d).

It is pointed out that, whereas step (b) has the purpose of locating elements (the wells) in the image, step (c) serves to interpret what the elements located represent. In fact, step (b) could yield a not completely correct result; i.e., it could identify as wells defects of the image or undesirable reflections of the surface of the cartridge not corresponding to wells. Thus, step (c) has the function of detecting which shapes identified in step (b) in actual fact correspond to wells of the cartridge.

According to a further aspect of the present invention, a cartridge for biochemical analyses is provided including: a supporting body, having a first face and a second face opposite to one another in a direction Z orthogonal to the first and second faces; a plurality of wells (e.g., ninety-six wells), in particular adapted to contain a solution for biochemical analyses; one or more biocompatible layers extending in respective wells; an anti-reflection layer extending over the first face outside said wells to generate destructive interference; and a layer extending within said wells to generate constructive interference. The latter layer and the biocompatible layer may coincide.

Furthermore, the cartridge may comprise an on-board containment module coupled to the first face of the supporting body (e.g., by gluing or clamping and the like) in outer edge regions of the first face for surrounding the plurality of wells completely.

According to a further aspect of the present disclosure, likewise provided is a kit, or system, for biochemical analyses comprising the optical analyzer and the cartridge described previously, which are designed to co-operate for supplying a result of the biochemical analysis.

There now follows a more detailed description of embodiments of the cartridge and of the optical analyzer, with reference to the respective figures.

FIG. 1-3 show a disposable cartridge for biochemical analyses, designated as a whole by the reference number 1. FIG. 1 is a top plan view of the cartridge 1, FIG. 2 is a bottom plan view of the cartridge 1, and FIG. 3 is a lateral cross-sectional view, taken along the line of section III-III of FIGS. 1 and 2.

The cartridge 1 comprises a supporting body 2 including a plurality of wells 8, an on-board containment module 3, a heater 5, and a temperature sensor 6, which form a microreactor for biochemical analyses. In what follows, the terms "cartridge" and "microreactor" are used interchangeably in so far as all the elements that make up the cartridge and the microreactor are obtained in integrated form using e.g., processes of micromachining on semiconductor material.

For simplicity, in what follows reference will be made to cartridges and instruments for the nucleic-acid amplification by PCR and the analysis of the results of amplification, without this implying any limitation. What is described hereinafter, in fact, finds advantageous application also in systems designed for execution and recognition of the results of different biochemical or chemical analyses, in addition to the process of amplification by PCR.

In one embodiment, the supporting body 2 is a chip of semiconductor material, for example monocrystalline silicon, and has a substantially rectangular shape. Furthermore, a face 2a of the supporting body 2 presents the plurality of wells 8, and is coated with a passivation layer 7 of biocompatible material, for example silicon oxide, BSA, sonicated salmon sperm DNA, and the like.

The on-board containment module 3 has e.g., in top plan view of FIG. 1, a closed polygonal shape and is made of preferably transparent polymeric material. The on-board containment module 3 is likewise fixed on the passivation layer 7 of the supporting body 2 in peripheral regions of the supporting body 2, for example by gluing using a biocompatible glue, in such a way as to surround the wells 8 completely without being superimposed thereon.

In detail, the cartridge 1 is used in a system for fluorescence analysis of biological or chemical specimens and is designed to house the aforesaid specimens. In this context, the transparency of the on-board containment module 3 is with respect to the excitation wavelengths and to the wavelengths generated by the fluorophores present in the specimen contained in the cartridge 1.

The wells 8 are designed to receive respective specimens of biological or chemical material for analysis. In one embodiment, the wells 8 number ninety-six (only some of which are illustrated in FIG. 1 for simplicity) and are arranged to form a matrix array having rows and columns. Each well 8 has e.g., a quadrangular shape, for example square with a side of 800 μm in length and a depth, measured in the direction Z, of 400 μm. Furthermore, each well 8 is separated from another well 8 immediately subsequent to it (along a same row and/or column of the array of wells) by a distance of between 200 and 500 μm. The wells could also be cylindrical, or any other suitable shape.

In general, each well 8 has a capacity between 100 nl and 300 nl, for example equal to about 200 nl. Due to the reduced dimensions of wells 8, and therefore of the reduced quantity of samples that each of them contains, the cartridge 1 is preferably made hydrophilic within the wells 8 and provided with an antireflective layer out of wells 8. Preferably, the inner walls and bottom of the wells 8 is covered with a layer adapted to generate constructive interference of a light beam, which illuminates the inner portion of the wells 8 (e.g., during fluorescence imaging).

In one embodiment, further, the cartridge 1 has been further functionalized in order to improve biocompatibility by fixing probes or protein or other ligand to the walls and/or to the bottom of the wells 8. The probes comprise, for example, single DNA strands complementary to target sequences being studied in the biological specimen. The protein can be, e.g., bovine serum albumin or BSA or antibodies.

The heater 5 and the temperature sensor 6 are made on a face 2b of the supporting body 2 opposite to the face 2a. In particular, the heater 5 includes a plurality of resistive coils designed to develop heat by the Joule effect when they are traversed by current. The coils of the heater 5 extend over the face 2b in regions of the face 2b substantially corresponding to respective regions of the face 2a that house the wells 8. The heater 5 and the temperature sensor 6 are thermally coupled to the wells 8 so that the thermal energy released by the heater 5 causes heating of the biological material in the wells 8. The heater 5 is defined by one or more conductive paths, for example, of metal or polysilicon. The temperature sensor 6 is of a thermoresistive type. As is known, in a thermoresistive sensor, the resistance varies as a function of the temperature, and thus a reading of the resistance indicates the temperature at a given moment in time.

The supporting body 2 further comprises contact pads 9a set at a longitudinal end of the supporting body 2 to form a connector 9. When the on-board containment module 3 is set on the face 2a of the supporting body 2, the connector 9 projects to one side with respect to the on-board containment module 3, outside the area enclosed by the on-board containment module 3. The connector 9 is electrically coupled to the heater 5 and to the temperature sensor 6 by conductive paths made of the supporting body 2. The connector 9 enables control of the supporting body 2 (e.g., for carrying out the thermal PCR cycles) once the supporting body 2 has been inserted into an analyzer (described hereinafter with reference to FIGS. 5 and 6).

To analyze a specimen with the cartridge 1, a mixture of reagents in solution that comprises fluorophores of two types is introduced into the wells 8. For instance, a first type of fluorophores (e.g., FAM fluorophores) has an excitation wavelength $\lambda E1$ and a detection wavelength (or emission wavelength) $\lambda D1$ and combines with a first substance being studied. A second type of fluorophores (e.g., ROX fluorophores) has an excitation wavelength $\lambda E2$ and a detection wavelength (or emission wavelength) $\lambda D2$ and combines with a second substance being studied or a control substance. The second type of fluorophores may have just the function of being a control marker, whereas the function of molecular probes for detecting the amplification of DNA is guaranteed by the fluorophores of the first type.

According to one aspect of the present disclosure, as illustrated in FIG. 3 in cross-sectional view, the passivation layer 7 has a thickness that varies according to whether it is measured in the wells 8 or else outside the wells 8. In greater detail, the passivation layer 7 has a thickness outside the wells 8, chosen to function as an anti-reflection layer for the excitation radiation used during the steps of detection of fluorescence. In this way, the surface of the cartridge 1 does not generate undesirable reflections. This problem is not posed inside the wells 8. On the contrary, within the wells 8 a constructive interference is preferably generated, to increase the intensity of the signal emitted by the wells 8. Thus, the portions of the passivation layer 7 external to the wells 8 are chosen with a thickness different from the portions of passivation layer 7 inside the wells 8.

In practice, to obtain a passivation layer 7 designed to function as anti-reflection layer outside the wells 8, it is expedient to consider the wavelength $\lambda_{E1}$ of the excitation radiation, the refractive index n of the material of which the passivation layer 7 itself is made (in the case where it is of silicon oxide ($SiO_2$), this value is approximately n=1.45), and the cosine of the angle θ that is formed with the normal to the plane of incidence of the radiation. The effective thickness h of the passivation layer 7, outside the wells 8, is thus chosen between $\lambda_{E1}$ cos θ/(4·n)−10% and $\lambda_{E1}$ cos θ/(4·n)+10%, preferably $\lambda_{E1}$ cos θ/(4·n).

The thickness h of the passivation layer 7, inside the wells 8, is chosen different from $\lambda_{E1}/(4·n)$, for example less than $\lambda E1/(4·n)$.

Furthermore, it may be noted that the passivation layer 7 of silicon oxide (treated e.g., with BSA) is biocompatible and thus suited to the use described.

According to an embodiment provided by way of example, the passivation layer 7 is made of $SiO_2$ and has a thickness inside the wells 8 of approximately 20 nm, and alongside the wells 8 (i.e., on the face 2a) of approximately 90 nm.

FIG. 4A-4D show schematically steps for manufacturing a cartridge 1 of the type described previously.

With reference to FIG. 4A, the supporting body 2 is provided (for example, a silicon substrate in the form of a wafer), having the face 2a opposite to the face 2b in the direction Z. On the face 2b, the supporting body 2 has the heater 5, the temperature sensor 6, and the connector 9, shown as contact pad 9a. These elements are formed by known steps, and thus their respective manufacturing steps are not described in detail.

Formed on the face 2a is a hard-mask layer 27, of silicon oxide ($SiO_2$), for example by thermal growth.

Then (FIG. 4B), there follows, in a known way and thus not described in detail, a step of masked etching of the hard-mask layer 27, for making openings 28 in the hard-mask layer 27 in the regions of the supporting body 2 in which it is desired to form the wells 8. The openings 28 expose respective surface portions of the face 2a.

Next (FIG. 4C), a further etch, using the hard-mask layer 27 as etching mask, enables removal of selective portions of the supporting body 2 at the openings 28. The plurality of wells 8 is thus formed (although in this step they are still lacking the layer of biocompatible silicon oxide). Etching of the silicon proceeds until the desired depth for the wells 8 is reached, for example 400 μm.

Finally (FIG. 4D), a step of thermal growth of silicon oxide ($SiO_2$) enables growth of a biocompatible layer 29 inside the wells 8 and on top of hard-mask layer 27. As an alternative to thermal growth, it is likewise possible to deposit silicon oxide, e.g., by chemical vapor deposition (CVD), molecular beam epitaxy (MBE), Solid Phase Epitaxy (SPE), Liquid Phase Epitaxy (LPE), and the like.

The thickness of the hard-mask layer 27 (in particular, after the step of further growth, or deposition, of FIG. 4D) is such as for being equal to $(\lambda_{E1}·\cos θ)/(4·n)$, as illustrated previously, or, more precisely an odd multiple of $(\lambda_{E1}·\cos θ)/(4·n)$, to prevent undesirable reflections according to what has been described previously. Instead, the thickness of the biocompatible layer 29 is different from $(\lambda_{E1}·\cos θ)/(4·n)$ and more precisely less than $(\lambda_{E1}·\cos θ)/(4·n)$.

The hard-mask layer 27 (as obtained after the etching step of FIG. 4B) together with the biocompatible layer 29 form the passivation layer 7 illustrated previously.

After step 4D, a step of gluing of the on-board containment module 3 is carried out using a biocompatible adhesive, for example silicone, to obtain the cartridge 1 of FIG. 3, although other attachment means such as rivets, clamps, welding and the like are possible.

In order to use the cartridge 1 in a real-time PCR analyzer, the wells 8 are further treated in order to improve the biocompatibility thereof.

The treatment comprises a step of cleaning and activation, and also includes a treatment using a solution of $CH_3OH$: HCl (4:1) for 10 minutes at room temperature, followed by a step of rinsing with ultra-pure water at pH 7.0 for removing the reagents in excess. This is followed by an anhydrification step comprising a thermal treatment in an oven for 15 minutes at 70° C.

These steps have the function of rendering the cartridge 1 (in particular, the wells 8) hydrophilic.

Then, the active surface of the wells 8 is further treated, during a blocking step, comprising a treatment using a solution including 1% BSA (bovine serum albumin), 5% SSC (sodium chloride plus sodium citrate). This step is performed, in particular, at 55° C. for a time of between 4 and 15 hours, where the solution is left to "rest" in the wells 8.

Finally, washing is carried out with deionized water.

Since the treatment that has been described previously to increase the hydrophilic nature may inhibit PCR on account of the presence of poly-electrolytes, the latter steps have the function of restoring characteristics suitable for PCR so that it may take place correctly and as desired.

Other surface treatments are possible, as needed for the application in question.

FIG. 5 shows a real-time PCR analyzer, designated as a whole by the reference number 10, designed for being used for reading the cartridge 1 described previously in order to acquire information on the state of the PCR.

Figure 6:
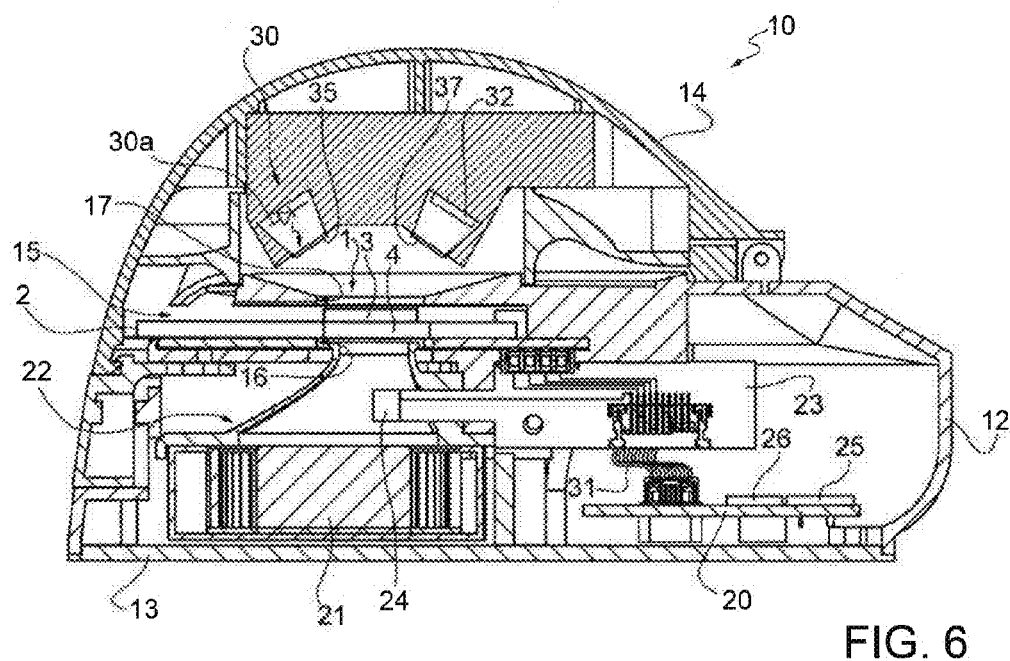
FIG. 6 is a lateral view, sectioned along a longitudinal plane, of the analyzer of FIG. 5.

As illustrated in FIGS. 5 and 6, the PCR analyzer 10 comprises a first shell 12, closed underneath by a metal plate 13, and a second shell 14, hinged to the first shell 12. The first shell 12, the metal plate 13, and the second shell 14 define a casing of the analyzer 10.

With reference also to FIG. 6, the first shell 12 has a slot 15 for receiving the cartridge 1. The slot 15 is accessible from outside for insertion of the cartridge 1 when the second shell 14 is open, in a raised position. In the region enclosed by the on-board containment module 3 inserted into the slot 15 (i.e., in a position corresponding to the wells 8), the first shell 12 has a first window 16 and a second window 17. The first window 16 sets the slot 15 in communication with the inside of the first shell 12, whereas the second window 17 enables observation of the wells 8 when the cartridge 1 is inserted into the slot 15 and the second shell 14 is raised.

Housed within the first shell 12 are a control board 20, a fan 21, a collector 22, and a sensor board 23, on which a calibrated temperature sensor 24 is mounted. The control board 20 and the fan 21 are fixed to the metal plate 13. The control board 20 houses a control unit 25, which presides over operation of the analyzer 10, as explained hereinafter, and at least one memory module 26.

In the embodiment described herein, the fan 21 is aligned to the windows 16, 17 and may be actuated for drawing in air through the collector 22. More precisely, a flow of air is drawn in along a path that develops from the slot 15 to the fan 21 through the collector 22 in such a way as to cause a heat exchange between the flow of air and the cartridge 1 set in the slot 15.

The second shell 14 is hinged to the first shell 12 and defines a lid, shaped for coupling in a light-tight way with the first shell 12 and obscuring the second window 17. In practice, when the second shell 14 is closed on the first shell 12, the inside of the second shell 14 is substantially inaccessible to environmental light, and the cartridge 1 inserted into the slot 15 is also obscured. When the second shell 14 is raised, the slot 15 is accessible for inserting and removing the cartridge 1. When the cartridge 1 is located in the slot 15, further, the wells 8 are visible and accessible from outside through window 17 to enable operations of loading of biological specimens for analysis.

Housed in the second shell 14 are a first light source 30, a second light source 31 (not visible in cross section of FIG. 6, but see FIG. 5), a first image sensor 32, and a second image sensor 33 (not visible in cross section of FIG. 6, but see FIG. 5), all operatively coupled to, and controlled by, the control unit 25.

The first light source 30 and the second light source 31, which comprise respective emitter devices 30a, 31a, for example of the LED type, are oriented for illuminating the cartridge 1 through the second window 17 and are provided, respectively, with a first excitation filter 35 and a second excitation filter 36 that intercept the radiation coming from the emitter device 30a and the emitter device 31a, respectively. The first excitation filter 35 and the second excitation filter 36 have respective excitation passbands $B_{E1}$, $B_{E2}$ centered around excitation wavelengths $\lambda_{E1}$, $\lambda_{E2}$ of fluorophores of two different types.

For instance, the first excitation filter 35 has a passband $B_{E1}$ centered around an excitation wavelength $\lambda_{E1}$ of 494 nm, i.e., compatible with FAM fluorophores, and the second excitation filter 36 has a passband $B_{E2}$ centered around an excitation wavelength $\lambda_{E2}$ of 575 nm, i.e., compatible with ROX fluorophores.

The light radiation supplied by the first light source 30 and by the second light source 31 is thus substantially confined, respectively, in the excitation passband $B_{E1}$ and in the excitation passband $B_{E2}$ of the first excitation filter 35 and of the second excitation filter 36. The excitation passbands $B_{E1}$, $B_{E2}$ are further separate and not overlapping.

The first image sensor 32 and the second image sensor 33, for example complementary metal-oxide-semiconductor or "CMOS" sensors, are arranged for receiving the light emitted by the fluorophores present in the specimen contained in the cartridge 1 and excited by the light coming from the first light source 30 and the second light source 31. In the embodiment described, in the case of FAM fluorophores, the wavelength of the radiation emitted is 516-522 nm (green), whereas, in the case of ROX fluorophores, the wavelength of the radiation emitted is 602 nm (red).

According to one embodiment, the first light source 30 and the first image sensor 32 are aligned along a first axis X, parallel to the plane of the supporting body 2 when the latter is located in the slot 15 and rotated through 45° with respect to a longitudinal axis of the supporting body 2 in the slot 15. The second light source 31 and the second image sensor 33 are aligned along a second axis Y, perpendicular to the first axis X and also rotated through 45°.

The first image sensor 32 and the second image sensor 33 are provided, respectively, with a first detection filter 37 and a second detection filter 38. The first detection filter 37 and the second detection filter 38 have respective detection passbands $B_{D1}$, $B_{D2}$ centered around detection wavelengths (or emission wavelengths) $\lambda_{D1}$, $\lambda_{D2}$ of the respective fluorophores. The passbands $B_{D1}$, $B_{D2}$ of the first detection filter 37 and the second detection filter 38 are further separate and not overlapping and exclude, respectively, the passbands $B_{E1}$, $B_{E2}$ of the first excitation filter 35 and of the second excitation filter 36.

In the embodiment described, further, the first image sensor 32 and the second image sensor 33 are RGB (red, green, blue) CMOS sensors and each supply three respective signals for the red, green, and blue channels. In fact, RGB CMOS sensors comprise a plurality of photodetectors arranged in an array and each provided with a respective red, green, or blue filter, with the green elements in a proportion twice that of the red and blue elements (RGGB), according to the so-called Bayer filter. An RGB sensor thus supplies three channel signals, or image signals, one for each of the fundamental colors red, green, and blue, which are then combined with local-average operators for reconstructing the original colors of the image acquired. Each image signal thus represents the same image filtered with a filter corresponding to one of the fundamental colors. In what follows, the term "image signals" $S_I$ will be understood as indicating all the channel signals regarding a same image or portion of image (possibly even a single pixel).

The signals supplied by the first image sensor 32 and by the second image sensor 33 thus contain information on the response of each type of fluorophore in the bands of the fundamental colors, when one or the other between the first light source 30 and the second light source 31 is activated.

The control unit 25 exploits the image signals $S_I$ and information preliminarily stored in the memory module 26 to determine the presence and concentrations (possibly zero) in the specimen of substances under investigation, to which the fluorophores are bound.

The control unit 25 presides over the operation of the analyzer 10 and controls execution principally of a thermal cycling to obtain amplification of the nucleic acids present in the biological material, for example by the PCR technique and a procedure of optical detection of specific sequences of nucleotides ("target DNA").

The cartridge 1 is inserted into the slot 15, and a solution containing a specimen of e.g., biological material and the ingredients for e.g., the amplification process is introduced into the wells 8. Among the other ingredients needed for PCR, the solution comprises nucleotides (G, A, T, C), primers, a DNA-polymerase enzyme (for example, TAQ-polymerase), $Mg^{++}$, fluorophores and probes containing single strand oligonucleotides.

In this step, no particular precision is required for introduction of the biological specimen and of the ingredients for the amplification process in so far as the on-board containment module 3 is sufficient to prevent said solution from flowing out of the cartridge 1. According to one aspect of the present disclosure, the solution and the ingredients for the amplification process are in liquid form and are introduced into the wells 8 with the aid of a soft brush (e.g., of hydrophobic polycarbonate). This step is sufficient to fill the wells 8 so that each of them contains approximately 200 nL of solution. To prevent the solution from evaporating, mineral oil may be used, which is introduced into the wells 8 for covering them completely. Also in this case, the on-board containment module 3 is designed to restrain the mineral oil, preventing it from coming out of the cartridge 1.

The control unit 25 drives the heater 5 and the fan 21, respectively, for supplying and subtracting thermal energy so that the temperature in the wells 8 varies cyclically according to a pre-set profile, which enables the reactions of amplification (in brief, denaturing, annealing, and extension followed by a hybridization step). If the specimen being analyzed contains sequences complementary to the probes, during the hybridization step fluorophores are incorporated in the hybridized strands, which are rendered optically detectable. Correspondence of the temperature with the desired profile is verified using the temperature sensor 6.

For the detection of hybridized strands, which contain fluorophores, the control unit 25 uses the procedure described hereinafter with reference to FIG. 7.

After a step of turning-on, with possible calibration (not described in detail), the control unit 25 acquires (step S1) both the image signal $S_I$ associated to the fluorophores of the first type (e.g., FAM fluorophores) with a detection wavelength $\lambda_{D1}$ (that respond to the excitation wavelength $\lambda_{E1}$ of the first light source 30) and the image signal $S_I$ associated to the fluorophores of the second type (e.g., ROX fluorophores) with a detection wavelength $\lambda_{D2}$ (that respond principally to the excitation wavelength $\lambda_{E2}$ of the second light source 31).

Figure 8:
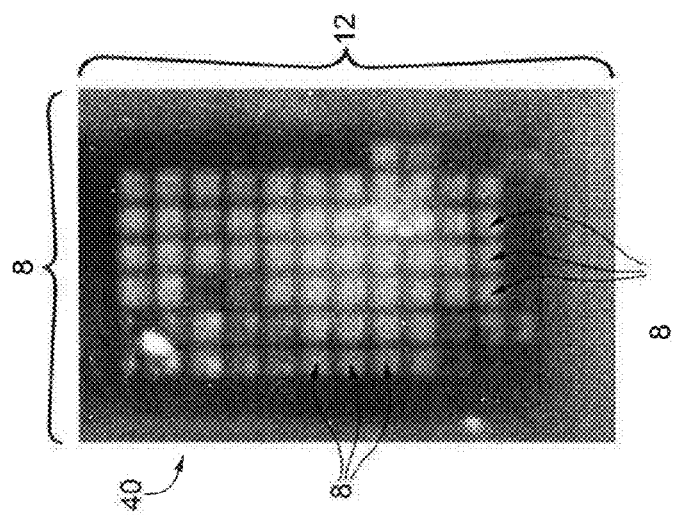
FIG. 8 shows an image of the cartridge of FIG. 1, acquired by the analyzer of FIG. 5.

The image signals $S_I$ thus obtained represent images defined by an array of dots (pixels). FIG. 8 shows, by way of example, an image 40 of a portion of the cartridge 1 in which the fluorescence radiation emitted by each well 8 is visible. In the sequel of the present description, reference will be made to the processing of just one image (e.g., the image associated to the fluorophores of the first type) provided by way of example. The same steps are carried out on the second image (e.g., the image associated to the fluorophores of the second type).

The brightness per single pixel is proportional to the power of fluorescence detected by the image sensors through the respective detection filters.

Next (step S2), the control unit 25 selects, in the image 40 of FIG. 8, regions of interest (ROIs), eliminating those portions of image devoid of significant information. In the embodiment described, in particular, the regions of interest selected correspond to the wells 8 of the cartridge 1. The step S2 is thus aimed at automatically recognizing the portions of the image 40 that include a well 8, excluding from processing the remaining portions that do not include a well 8. The wells 8 are isolated in the image 40 to identify the boundary thereof. Consequently, this step comprises processing of the image 40 for carrying out an edge detection of the elements present in the image 40.

Known in the state of the art are numerous edge-detection techniques starting from a generic image. These techniques are used in order to detect the points of a digital image in which the light intensity undergoes a variation above a certain threshold. Sharp changes of light intensity of an image typically identify significant changes of the physical reality that the image represents. With reference to the image 40 of FIG. 8, a high light intensity of the image corresponds to the area delimited by the wells 8 that emit fluorescent radiation. The edge-detection operation generates an image containing much less information than the original image 40, since details that are not relevant for the purposes of boundary identification are eliminated, conserving, instead, the information essential for describing the geometrical characteristics of the wells 8.

Known edge-detection methods comprise search-based methods and methods based upon zero-crossing. Search-based methods recognize the boundaries seeking the maxima and the minima of the first-order derivative of the image, typically identifying the direction in which there is the maximum local gradient. Zero-crossing methods seek the points in which the second-order derivative crosses the zero value.

Figure 7:
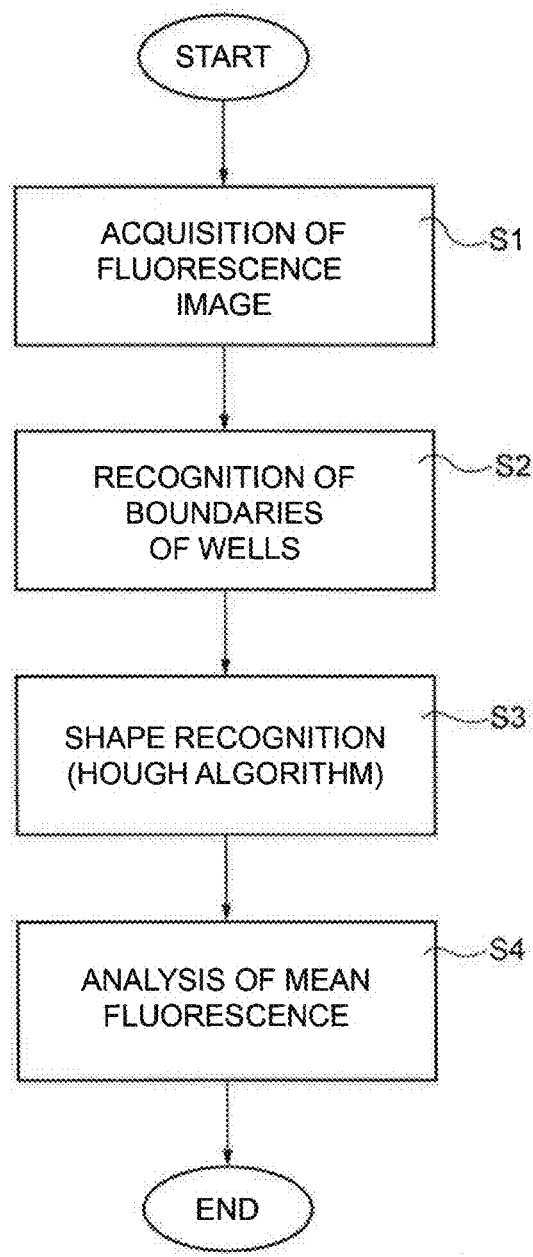
FIG. 7 is a flowchart regarding a method for acquiring images of the cartridge of FIG. 1-3 by the analyzer of FIG. 5-6 in order to carry out steps of the biochemical process, according to an embodiment of the present invention.

One of the known methods that may be used for the present disclosure to implement step S2 of FIG. 7 is known as Canny algorithm, or Canny method (J. F. Canny, "A computational approach to edge detection, IEEE Trans., Pattern Analysis and Machine Intelligence, 8(6), 1986, 679-698).

Figure 9:
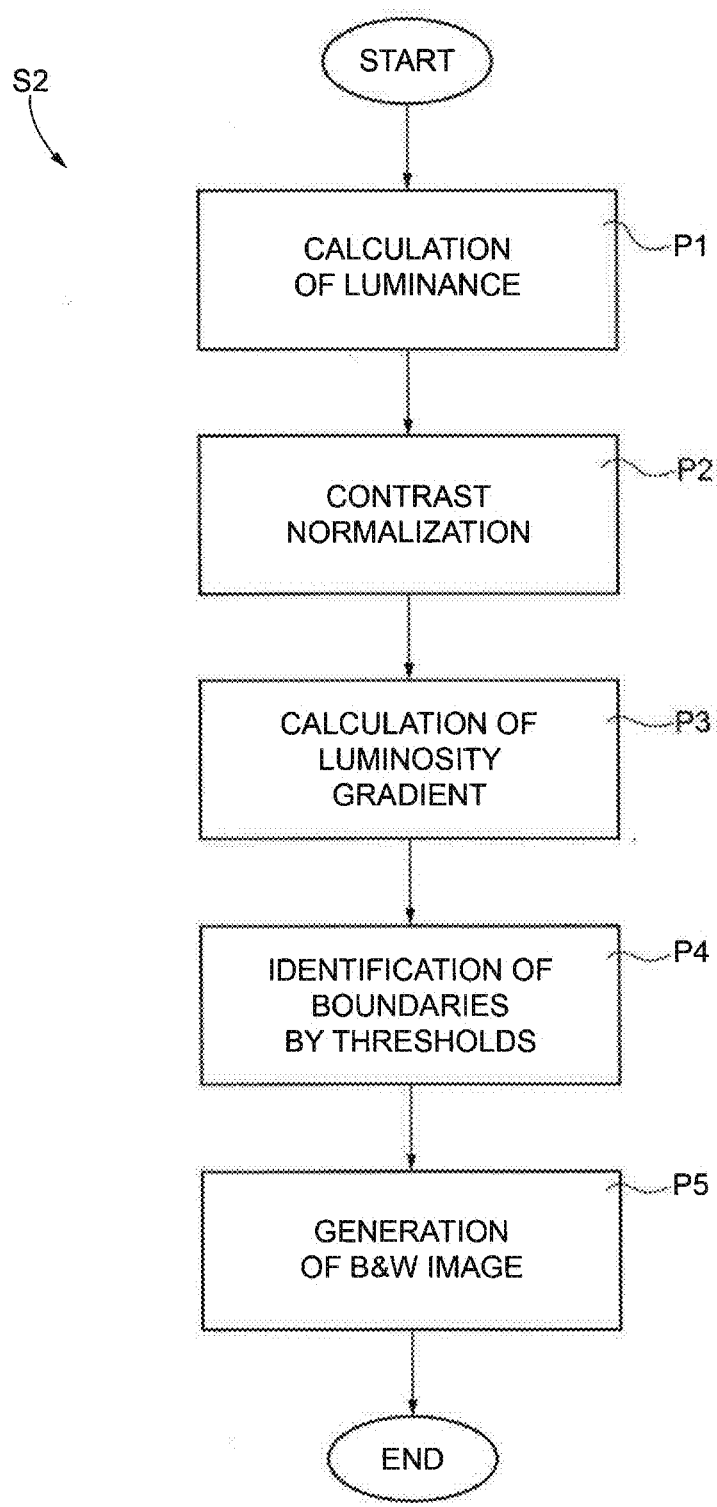
FIG. 9 is a flowchart regarding a method for processing the image of FIG. 8 in order to identify wells belonging to the cartridge of FIG. 1 represented in the image of FIG. 8.

For completeness of description, there are now described, with reference to FIG. 9, sub-steps that implement, according to one aspect of the present disclosure, an edge-detection method according to step S2 of FIG. 7. The method of FIG. 9 may be implemented on a computer using a software program.

With reference to FIG. 9 (step P1), the image 40 acquired (in digital format) is processed for detecting values of luminance. Luminance is defined as the photometric measurement of light intensity per unit area. The choice of the value of unit of area A for being considered is the fruit of assessments deriving from the particular case under examination, such as for example the size of the image and the desired precision.

According to one aspect of the present disclosure, the image 40 has dimensions of 300×200 pixels, and the unit of area chosen for calculation of the luminance is one pixel; namely, the value of luminance of the image 40 is calculated for each pixel. For this purpose, there is acquired, for each i-th pixel, the value of red $R_i$ (in the range 0-255), of green $G_i$ (in the range 0-255), and of blue $B_i$ (in the range 0-255), and the respective value of luminance $L_v$ is obtained by applying the following equation:

$$L_{v\_i} = 0.2126 \cdot R_i + 0.7152 \cdot G_i + 0.0722 \cdot B_i$$

It is pointed out that the values 0 and 255 are, respectively, the minimum value and the maximum value allowed for each pixel represented on 8 bits. Other ranges may be used, however.

An array having the same size in pixels of the image 40 is thus generated (e.g., a 300×200 matrix or a vector having 60 000 locations), where each field identifies a value of luminance of the respective pixel.

Then (step P2), a first processing of the image of FIG. 8 is carried out, normalizing the value of contrast pixel by pixel. For this purpose, the values of red, green, and blue for each pixel are extrapolated from the image 40, as described with reference in the previous step P1. Thus, for each i-th pixel, there are obtained the values of red $R_i$ (in the range 0-255), green $G_i$ (in the range 0-255), and blue $B_i$ (in the range 0-255). For each i-th pixel, an operation of normalization is carried out, for each color component, according to the formula:

$$C_i = ((R_i + G_i + B_i)/3)$$

where $C_i$ is the respective color component ($C \in \{R,G,B\}$) with respect to which normalization is carried out.

An array having the same size in pixels of the image 40 (e.g., a 300×200 matrix, or a vector with 60,000 locations) is thus obtained, where each field identifies a normalized value of contrast for that respective pixel. This step is optional and has the function of reducing the possible presence of noise in the image.

Then (step P3), values of gradient of brightness of the image obtained in step P2 are calculated using a Gaussian filter. It is thus expedient to specify the dimensions of the Gaussian filter, which affect directly the result of the operation. As is known, Gaussian filters of small dimensions (small radius) enable recognition of clearer boundaries at the expense of the processing rate, whereas filters of large dimensions (large radius) guarantee greater rapidity of execution but are indicated for recognizing wider and fuzzier boundaries.

The present applicant has found that a good compromise, for the particular case forming the subject of the present disclosure, is obtained by choosing a value of Gaussian-kernel radius of 3 and a value of Gaussian-kernel width 5.

Within the area defined by the values chosen for the radius and for the width of the Gaussian function, the variation of intensity of the light is acquired, pixel by pixel. Following upon step P3, a map of gradients is obtained that supplies the value of amplitude of the gradient for each pixel of the image 40 and the direction of the gradient. The value of the gradient, together with an array of values of the modulus (or magnitude) of the gradient are used as input parameters for defining the thresholds for use in the thresholding process of the subsequent step P4. A value of local maximum indicates a high probability of presence of a portion of a boundary sought. However, this indication is not sufficient to decide whether a given region corresponds to a boundary region of a well 8 or else to a central portion thereof. The points corresponding to the local maxima are considered as belonging to a boundary and will be taken into consideration in the subsequent processing steps. There is a local maximum in the points where the derivative of the gradient goes to zero.

At the end of the step of searching for local maxima, the resulting image is defined by an array containing values of levels of grey that represent possible edge pixels of each well 8. It is thus expedient to carry out a decision step to decide which pixels effectively represent an edge.

Then (step P4), identification of the boundaries is carried out by thresholding with hysteresis. For this purpose, two thresholds are defined: a lower threshold T1 and an upper threshold T2, which are compared with the gradient calculated for each pixel. If the value of the gradient is less than the lower threshold T1, the pixel is rejected; if the value of the gradient is higher than the upper threshold T2, the pixel is accepted as part of a boundary; if the value of the gradient is between the two thresholds T1 and T2, the pixel is accepted only if it is contiguous to a point already accepted previously.

The presence of two thresholds T1 and T2 solve the difficulty that would arise in defining a single value of gradient of brightness to discriminate whether a pixel belongs to a boundary. It is evident that the values of T1 and T2 may be chosen case by case, on the basis of the image that is being analyzed. By way of example, the present applicant has found that acceptable values are T1=100 and T2=190. These values are compared with the value of gradient of brightness detected in the previous step P3 (i.e., the comparison is carried out for each measurement of gradient, on the array of pixels). The range of possible values for the gradient, calculated on the specimen image of FIG. 8, is between 0 and 255.

At the end of this step P4, a binary image is obtained, where each pixel is marked as belonging to a boundary or else not belonging to a boundary.

Then (step P5), a step of generation of the binary image (i.e., represented with just two colors, or just two levels of brightness) is carried out, where the boundary pixels are represented in white (or black) and the remaining pixels are represented in black (or white). There is thus obtained an image of the type illustrated in FIG. 10 and designated by the reference number 50. The image 50 is a binary image, i.e., represented on just two levels of color (black and white), where the information associated to a dot (pixel) is represented only by its position.

Figure 10:
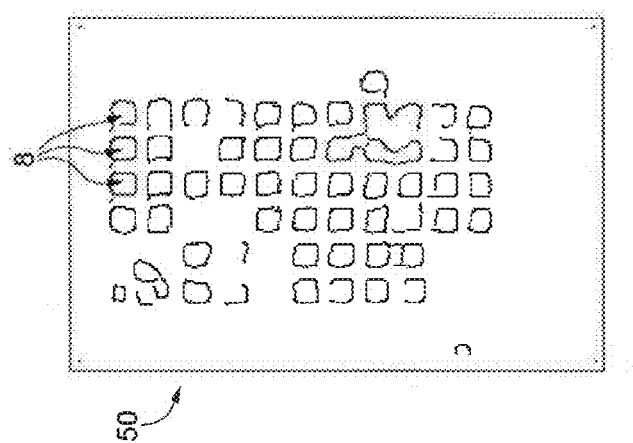
FIG. 10 shows the image of FIG. 8 after the processing steps of FIG. 9.

To return to the steps of the method of FIG. 7 (step S3), a pattern-recognition algorithm is applied to the image 50 of FIG. 10. An example of algorithm that may be used is known as the Hough algorithm.

In this context, pattern recognition is based upon maximum-likelihood estimations, and not on an exact correspondence. In other words, statistical variations are taken into account in so far as the wells represented in the image 50 do not have an ideal quadrangular shape. By way of example, it is possible to use the Hough algorithm, or any other known pattern-recognition algorithm, for example Radon algorithm (or transform, or filter).

In what follows, explicit reference will be made to the Hough transform (also referred to as "Hough filter" or "Hough algorithm"), without this implying any loss of generality.

The Hough algorithm is a method, in a per se known manner, used for identifying shapes defined analytically (lines, circles, polygons, etc.) within a digital image.

The Hough algorithm is founded on the assumption that each dot (pixel) provides a contribution (also referred to as "vote") to the definition of a space different from that of the image, referred to as "parameter space" or "accumulator" (in the case of the image 50, the space is two-dimensional, which may be represented by an accumulation vector or matrix, or "array").

The Hough algorithm receives as input the co-ordinates of the points belonging to the curve present in the image (i.e., of the pixels identified as belonging to a boundary), and supplies as output a parametric description of the set of the curves recognized, belonging to a fixed analytical figure (as has been said, a line, a polygon, etc.).

In detail, once the analytical figure that is for being sought has been defined and parameterized (e.g., a straight line), for each pixel detected within the image 50 all the curves that could pass through that pixel are identified (in the case of a search for a straight line, the set of the possible curves is the sheaf of straight lines passing through the pixel), and the corresponding locations of the accumulation array are incremented accordingly.

An accumulation function is thus obtained, which is defined in the parameter space and the maxima of which determine the parameters that identify the curves identified in the image space.

In the case of recognition of lines, the analytical description adopted is not the parametric form $y=mx+b$, but, for computational reasons, a representation in polar co-ordinates of the type $\rho=x\cdot\cos\theta+y\cdot\sen\theta$ is used, where the parameters for being identified are the pair $(\rho, \theta)$, where $\rho$ is the distance between the straight line and the origin of the reference system and $\theta$ is the angle that the normal to the straight line forms with the positive x semi-axis.

The accumulation matrix $A_{(\rho,\theta)}$ represents the space in polar co-ordinates $(\rho,\theta)$. For each pixel in the space of the starting image 50, all the curves are calculated that pass through that pixels and the corresponding cells of the accumulation matrix $A_{(\rho,\theta)}$ are incremented. The points of maximum of the accumulation function thus obtained determine the straight lines sought.

Starting from equalization of one or more straight lines, it is possible to identify different geometrical shapes or else identify the points of intersection between the straight lines, thus identifying a characteristic point of each well 8.

Further known in the literature is the generalized Hough transform, whereby, given a geometrical shape for being identified, if the image analyzed contains instances of the shape for being identified, the votes accumulate in the positions of the reference point that corresponds to said instances. As in the classic Hough transform, the peak of the accumulator is sought, and said peak represents the instance of the shape sought. The method described presupposes that the shapes have the same size and orientation, but further generalizations are known also in the cases of variation of scale and orientation.

For instance, with reference to the image 50 of FIG. 10, it is possible to use, as input to the function that implements the Hough transform, the image 50 as an image on which to carry out the search for the geometrical shapes for being identified and an ideal reference image that represents each well 8. For instance, the reference image is a square, for example of 14×14 pixels in size. In this way, by applying the generalized Hough transform, an image 60 of the type illustrated in FIG. 11 is automatically obtained, where each instance (the wells 8) of the image 50 deemed comparable and affine (on the basis of processing of the Hough transform) with the reference image of FIG. 11 has been identified.

The Hough transform also yields a pair of values $(p_i, q_i)$ for each well 8 identified in the image 60, identifying a pair of co-ordinates belonging to the respective well 8 (for example, this pair of co-ordinates identifies a respective vertex of each well 8). In this way, it is possible to know exactly the position of each well 8 in the image 60 and, consequently, in the original image 40.

Figure 11:
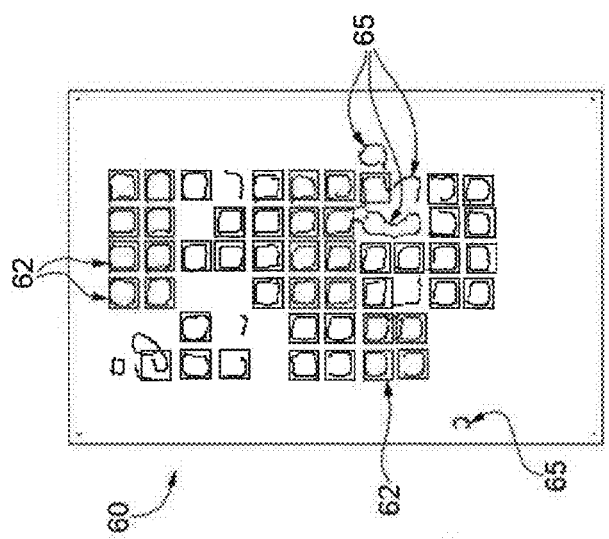
FIG. 11 shows the image of FIG. 9 at the end of the processing steps of FIG. 7.

FIG. 11 shows an image 60 that is obtained starting from the image 50 of FIG. 10, where the shapes that, on the basis of the previous steps, have been identified as resembling the ideal reference image, have been surrounded by a square 62 that is precisely the aforesaid ideal reference image. Other shapes (e.g., the rounded shapes designated by the reference 65), unlike the ideal reference square 62, have not been identified as wells 8 and thus will not be taken into consideration during the subsequent step S4.

Next (step S4 of FIG. 7), the fluorescence of the wells 8, as this may be detected from the image 40, is analyzed. This step is performed by calculating the values of light intensity of the pixels of the image 40 exclusively at the wells 8 identified during the previous step S3, i.e., in regions of the image 40 corresponding to respective regions of the image 60 internally delimited by the ideal reference squares. More in particular, this step comprises calculating the mean light intensity at the wells represented in the image 40.

For this purpose, therefore, the value of light intensity is calculated pixel by pixel (as has been said, only for the wells selected), the values thus calculated are added to one another, and an operation of division by the total number of pixels considered is carried out (in other words, an operation of arithmetic average is performed). The light intensity of the fluorescence emitted by each well of the image 40 is thus given by the sum of the values of light intensity of the pixels of each well identified, divided by the number of pixels, and identifies the value of fluorescence emitted by each well 8 of the cartridge 1 at the instant of analysis considered.

Consequently, it is possible to determine the concentrations of the emitting fluorophores in the specimen under examination, for example by thresholds.

The concentrations thus determined are stored in the memory module 26, possibly processed by the control unit 25, and made available through an interface (not illustrated), for example a USB interface.

By carrying out the steps S1-S4 of FIG. 7 a number of times during the PCR thermal cycles it is possible to glean information on the plot of the fluorescence signal and, consequently, information on the PCR itself.

It is known that, in a typical PCR, the PCR product increases at each amplification cycle, and the diagram of the fluorescence over the number of cycles exhibits a sigmoidal plot. In the final cycles, the PCR products no longer increase, and the curve presents a plateau. Thus, by tracing a curve of interpolation of the mean-fluorescence values obtained by repeating the steps of FIG. 7 a number of times it is possible to acquire information regarding the success of amplification (the curve is substantially a sigmoid) or otherwise to obtain an indication that the amplification procedure has not been successful.

The same steps of FIG. 7 are likewise carried out for acquiring the fluorescence emitted by the reference fluorophores (ROX fluorophores) in order to carry out a check with reference fluorophores.

The passivation layer 7 with variable thickness enables an effective reduction of the reflection of the excitation radiation at the level of the supporting body 2, preventing or reducing considerably any imprecision in reading due to undesirable reflections. The advantage is particularly important for portable analyzers, which, in order for being readily transportable and usable even outside the laboratory, must be reduced in dimensions and weight, as well as presenting a low cost. In particular, owing to the constraints imposed by the applications it is difficult and economically not advantageous to adopt solutions that might allow optimization of the uniformity of the radiation detected at the level of the analyzer.

According to a further aspect of the present disclosure, there now follows a description of a procedure for in-vitro diagnosis of genetic illnesses (FIG. 13) starting from biological specimens directly taken from the subject undergoing examination (in particular, specimens of saliva taken with a swabs), directly automated, in a single step.

Figure 12:
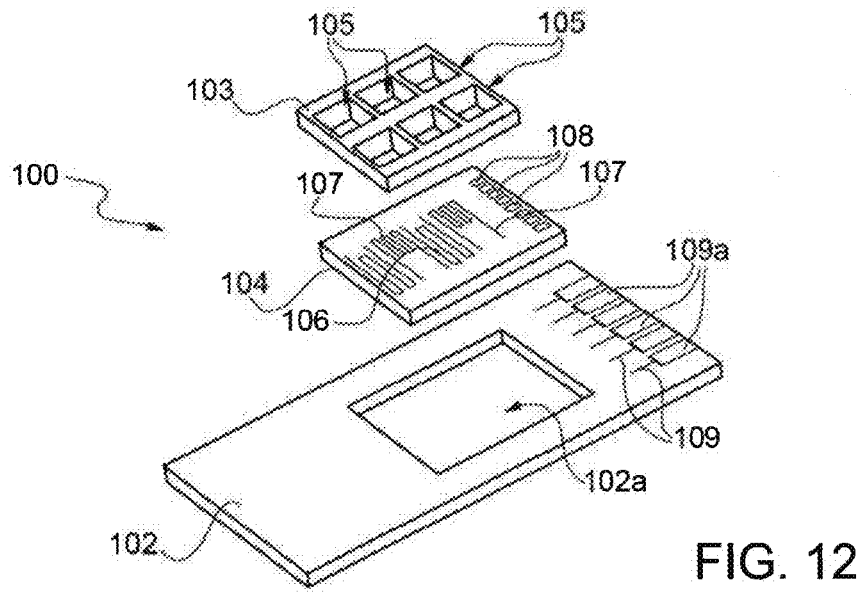
FIG. 12 shows an exploded perspective view of a microreactor for biochemical analyses of a known type.
Figure 13:
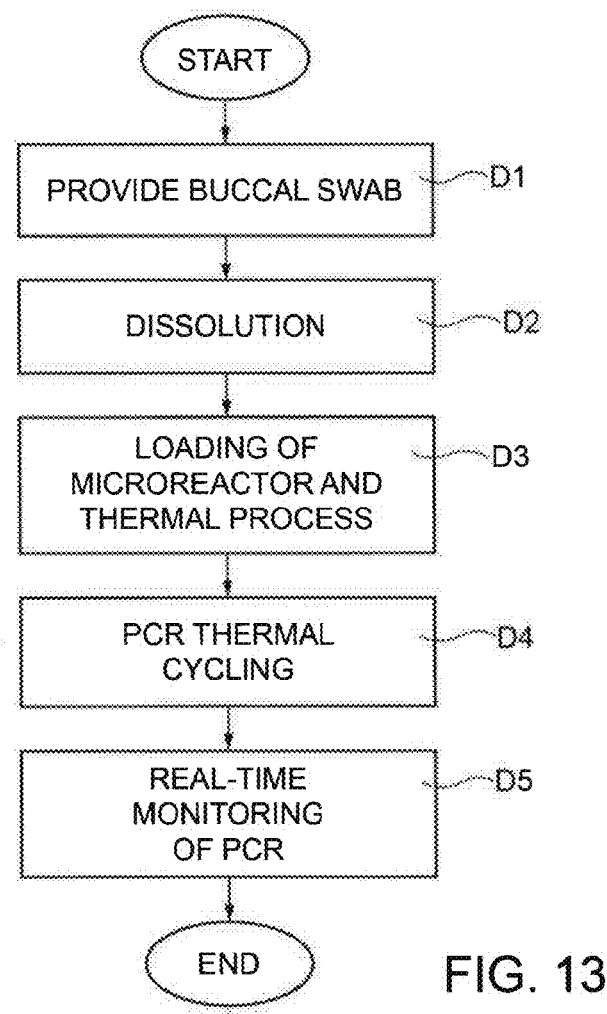
FIG. 13 shows a diagnostic method that may be implemented by a kit including the microreactor of FIG. 12 and the analyzer of FIGS. 5 and 6.

The procedure of FIG. 13 applies, in a particular way, to a cartridge or microreactor for biochemical analyses of the type described in the document No. US20130004954, filed in the name of STMicroelectronics s.r.l., and illustrated in FIG. 12.

Alternatively, it is also possible to use a cartridge or microreactor for biochemical analyses of the type described in the document No. US20130004952, filed in the name of STMicroelectronics s.r.l.

However, other cartridges or microreactors may be used, preferably including wells of a square or rectangular shape having, in top view, sides of dimensions equal to or greater than 1 mm. Alternatively, the wells may have a circular shape in top view, with a diameter equal to or greater than 1 mm.

The exploded view of FIG. 12 shows a cartridge, or microreactor, 100 for biochemical analyses of the type described in US20130004954. The microreactor 100 is housed on a printed-circuit board (PCB) 102. More precisely, the PCB 102 has a through opening 102a, where the microreactor 100 is housed. The microreactor 100 comprises a first chip 103, for example of polymeric material, and a second chip 104, of semiconductor material (for example, silicon) joined together, for example by a silicone-based adhesive.

A plurality of wells 105 are made in the first chip 103 and are configured to receiving solutions containing biological specimens for being analyzed. In one embodiment, the microreactor 100 has been functionalized by fixing DNA probes to the walls or bottom of the wells 105. The DNA probes may comprise single DNA strands containing sequences complementary to the target nucleotides of interest in the biological specimen.

Integrated in the second chip 104 are heaters 106 and on-board temperature sensors 107. The on-board temperature sensors 107 are of a thermoresistive type. In practice, their resistance varies as a function of temperature and thus a reading of the resistance indicates the temperature at any given instant. The second chip 104 projects slightly on one side with respect to the first chip 103 and on the projecting part houses contact pads 108 for connection of the heaters 106 and of the on-board temperature sensors 107 with conductive paths 109 on the PCB 102. Terminals 109a of the paths 109 enable connection of the PCB 102 once it has been inserted into a PCR analyzer.

The microreactor 100 comprises, according to one embodiment, six wells 105 having a substantially square or rectangular shape, in top plan view. Each well 105 has, for example, sides of between 3 mm and 4 mm in length, and a depth of approximately 3 mm. Furthermore, each well 105 is separated laterally from another well 105 by a distance of approximately 1 mm. Of course, 6 wells are shown for simplicity, but the device can contain additional wells, such as 12, 24, 48 or 96 wells.

With reference to FIG. 13, according to the procedure of diagnosis of genetic illnesses of the present disclosure, a first step D1 is carried out in which a specimen of buccal swab is provided. The swab specimen may be acquired by simple sampling of cells of the buccal epithelium, following a non-invasive procedure, then dispersing (step D2) the epithelial cells in a transport medium of a known type (dissolving step).

The dissolving step dissolution of the specimen cells taken in a transport medium (or transport solution). The transport solution is designed to favor lysis of the epithelial cells taken for releasing the DNA. Lysis is completed during the initial steps of the thermal cycling of the subsequent steps (favored by heat).

For this analysis, each well 105 of the microreactor 100 is pre-loaded (step D3) with:

- 27 µl of wax (which is melted and poured into each well 8), and this serves to seal each well 8 to prevent evaporation during the PCR thermal cycling;
- 4 µl of reagents for PCR (including primers, probes, and polymerase enzyme), in the form of a liquid solution; and
- 2 µl of solution containing the epithelial cells dissolved in the transport medium.

The wax used may be compatible with PCR and with the reagents used; in particular, it must not inhibit PCR. Furthermore, when molten, it may be transparent and exhibit a low fluorescence at the wavelengths of interest (used for fluorescence analysis) in order not to interfere with the measurements of the fluorescence emitted by the wells 8. Furthermore, it must preferably present a low vapor tension so as not to evaporate during the thermal cycles required for PCR.

Preferably, it must have a density lower than the density of the PCR reagents and of the solutions used in such a way that it will cover the PCR reagents and the solution in order to prevent their evaporation during the PCR thermal cycles. This further enables introduction into the wells 8 of PCR reagents/solution for analysis independently before or after insertion of the wax into the wells 8 (the wells 8 may thus be pre-loaded with the wax during the steps for manufacturing the cartridge 1 themselves). Furthermore, the wax enables an effective and valid protection of the wells 8, thus preventing phenomena of cross-contamination between adjacent wells 8 and from external contaminating agents. Furthermore, the wax used must have an adequate melting temperature so that it is solid at a room temperature (or temperatures lower than room temperature), but liquid at the temperatures at which PCR is conducted (typically equal to or higher than approximately 55° C.).

Applicants have found that a wax that possesses the above characteristics is a paraffin wax, in particular of the type marketed by Sigma-Aldrich with the code 76228. As an alternative to wax, it is also possible to use mineral oil.

Then (step D4), the microreactor 100 thus loaded is inserted into the analyzer (e.g., the analyzer 10 of FIG. 5 or the analyzer described in the document No. US 2013/0004954), and the PCR thermal cycling is started.

For this purpose, by way of example, the thermal cycling comprises heating to a temperature chosen in the range of 94 to 99° C. for a time of between 2 and 10 minutes, and then a plurality of cycles (e.g., fifty cycles), where each cycle includes:
- a step of heating to a temperature of between 94 and 99° C. for a time of between 5 and 20 seconds; and
- a step of heating to a temperature of between 57 and 62° C. for a time of between 35 and 70 seconds.

During these thermal cycles, the PCR process is monitored (step D5) by fluorescence analysis, for example according to what has been described previously, by carrying out the steps S1-S4 of FIG. 7. However, any other real-time monitoring method of a type known to the state of the art may be used (for example, as described in the document No. US20130004954).

Modifications and variations may be made to the device and to the method described herein, without thereby departing from the scope of the present invention, as defined in the attached claims.

The invention claimed is:

1. A cartridge for an optical analysis, comprising:
   a) a supporting body, having a first face and a second face opposite to one another;
   b) a plurality of wells adapted to receive a biological solution to be analyzed, said wells extending in said supporting body on said first face;
   c) at least one biocompatible layer extending inside each well;
   d) an anti-reflection layer extending on said first face outside and exterior to said wells; and,
   e) a reflection layer extending inside each well, wherein together said biocompatible layer, said anti-reflection layer and said reflection layer define a passivation layer, wherein said passivation layer is composed of varying thicknesses.

2. The cartridge according to claim 1,
   wherein said anti-reflection layer has:
   a thickness of approximately one quarter of an excitation wavelength (XE1) divided by a refractive index of the anti-reflection layer, or a thickness equal to an odd multiple of one quarter of the excitation wavelength divided by the refractive index of the anti-reflection layer, and multiplied by the cosine of an angle that is formed with a normal to a plane of incidence of a radiation having the excitation wavelength (XEI), and
   wherein said reflection layer has a thickness smaller than one quarter of the excitation wavelength (XE1) divided by a refractive index of the biocompatible layer and multiplied by the cosine of the angle that is formed with the normal to the plane of incidence of the radiation having the excitation wavelength (XE1).

3. The cartridge according to claim 2, wherein said reflection layer and said biocompatible layer coincide.

4. The cartridge according to claim 1, wherein said biocompatible layer, said reflection layer and said anti-reflection layer are made of silicon oxide.

5. The cartridge according to claim 1, where said at least one biocompatible layer includes a silicone oxide layer covered with Bovine Serum Albumin.

6. The cartridge according to claim 1, further comprising an on-board containment module coupled to the first face of the supporting body at edge regions of the first face for completely surrounding said plurality of wells.

7. The cartridge according to claim 1, further comprising at least one heater thermally coupled to the plurality of wells by the supporting body.

8. The cartridge according to claim 1, further comprising a temperature sensor thermally coupled to the supporting body.

9. The cartridge according to claim 2, wherein each well of said cartridge comprises nucleic-acid probes for hybridization to respective target nucleic acids, and a solution containing two primers capable of binding to a target nucleic acids, nucleotides, nucleic-acid extender enzymes and said target nucleic acids, and said solution being uniformly covered by mineral oil for countering evaporation of said solution.

10. A method of manufacturing a cartridge for an optical process, comprising:
   forming a plurality of wells adapted to receive a sample to be analyzed in a supporting body having a first face and a second face opposite to one another, said wells extending in said supporting body on said first face;
   forming at least one biocompatible layer extending inside each well;
   forming an anti-reflection layer extending on said first face outside and exterior to said wells; and,
   forming a reflection layer extending inside each well, wherein together said biocompatible layer, said anti-reflection layer and said reflection layer define a passivation layer, wherein said passivation layer is composed of varying thicknesses.

11. The method according to claim 10,
   wherein said anti-reflection layer has:
   a thickness of approximately one quarter of an excitation wavelength (XE1) divided by a refractive index of the anti-reflection layer, or a thickness equal to an odd multiple of one quarter of the excitation wavelength divided by the refractive index of the anti-reflection layer, and multiplied by the cosine of an angle that is formed with a normal to a plane of incidence of a radiation having the excitation wavelength (XEI), and
   wherein said reflection layer has a thickness smaller than one quarter of the excitation wavelength (XE1) divided by a refractive index of the biocompatible layer and multiplied by the cosine of the angle that is formed with the normal to the plane of incidence of the radiation having the excitation wavelength (XE1).

12. The method according to claim 10, further comprising the step of rendering the biocompatible layer hydrophilic.

13. The method according to claim 12, wherein rendering the biocompatible layer hydrophilic includes:
   depositing a silicon dioxide layer in said wells;
   treating the silicon dioxide layer using a solution of $CH_3OH:HCl$;
   rinsing the treated silicon dioxide layer with water; and,
   carrying out an anhydrification step.

14. The method according to claim 13, wherein treating the silicon dioxide layer using a solution of $CH_3OH:HCl$ comprises treating the silicon dioxide layer using a solution of CH3OH:HCl (4:1) for 10 minutes at room temperature; wherein rinsing comprises rinsing with ultra-pure water at pH 7.0 for removing excess reagents; and, wherein the anhydrification step comprises a thermal treatment in an oven for 15 minutes at 70° C.

15. The method according to claim 10, wherein the steps of forming said reflection layer and said biocompatible layer are carried out in single step deposition step.

16. The method according to claim 10, wherein forming said biocompatible layer, said reflection layer and said anti-reflection layer includes depositing silicon oxide.

17. The method according to claim 10, wherein forming at least one biocompatible layer includes:
depositing a silicon dioxide layer in said wells; and
treating said dioxide layer with a solution including 1% bovine serum albumin, 5% sodium chloride plus sodium citrate.

18. The method according to claim 17, wherein said treating step is performed at 55° C. for a time of between 4 and 15 hours, the method further comprising washing with deionized water.

19. The method according to claim 10, further comprising forming an on-board containment module coupled to the first face of the supporting body at edge regions of the first face for completely surrounding said plurality of wells.

20. The method according to claim 10, further comprising forming at least a heater thermally coupled to the plurality of wells of the supporting body.

21. The method according to claim 10, further comprising forming a temperature sensor thermally coupled to the supporting body.

22. A method of PCR analysis, said method comprising:
providing a cartridge for an optical analysis, the cartridge including:
a supporting body, having a first face and a second face opposite to one another;
a plurality of wells adapted to receive a biological solution to be analyzed, said wells extending in said supporting body on said first face;
at least one biocompatible layer extending inside each well;
an anti-reflection layer extending on said first face outside and exterior to said wells; and,
a reflection layer extending inside each well, wherein together said biocompatible layer, said anti-reflection layer and said reflection layer define a passivation layer, wherein said passivation layer is composed of varying thicknesses;
adding nucleic-acid probes to each well of the cartridge;
adding a solution containing two primers capable of binding to a target nucleic acid, nucleotides, nucleic-acid extender enzymes and a sample nucleic acid containing a target nucleic acid to each of said wells;
performing a plurality of thermal cycles in said wells to amplify said target nucleic acid; and
detecting hybridization of said amplified nucleic acid to said nucleic acid probes in each of said wells.

23. The method according to claim 22, further comprising the step of:
covering said wells with wax or mineral oil during said thermal cycles.

24. The method of claim 22, wherein said detecting step d occurs in each thermal cycle.

25. The method according to claim 22, further comprising the steps of:
supplying a sample biological specimen; and
extracting, from said sample biological specimen said sample nucleic acid.

* * * * *